United States Patent
Chazan et al.

(10) Patent No.: US 7,278,291 B2
(45) Date of Patent: Oct. 9, 2007

(54) TRACE GAS SENSOR WITH REDUCED DEGRADATION

(75) Inventors: David J. Chazan, Palo Alto, CA (US); David J. Anvar, Sunnyvale, CA (US); Autumn Talbott, San Francisco, CA (US)

(73) Assignee: Apieron Biosystems Corp., Menlo Park, CA (US)

(*) Notice: Subject to any disclaimer, the term of this patent is extended or adjusted under 35 U.S.C. 154(b) by 0 days.

(21) Appl. No.: 11/348,925

(22) Filed: Feb. 6, 2006

(65) Prior Publication Data

US 2006/0191321 A1    Aug. 31, 2006

Related U.S. Application Data

(63) Continuation-in-part of application No. 11/053,046, filed on Feb. 7, 2005, now abandoned.

(51) Int. Cl.
*G01N 7/00* (2006.01)
*G01N 9/00* (2006.01)

(52) U.S. Cl. .................... 73/31.05; 73/23.2
(58) Field of Classification Search ......... 73/23.2, 73/31.05
See application file for complete search history.

(56) References Cited

U.S. PATENT DOCUMENTS 5,096,813 A * 3/1992 Krumhar et al. ............ 435/28
5,421,981 A    6/1995 Leader et al.
5,795,187 A    8/1998 Sipe
6,010,459 A    1/2000 Silkoff et al.
6,787,366 B1 * 9/2004 Novak ..................... 436/162
2004/0017570 A1    1/2004 Parikh et al.
2004/0104114 A1    6/2004 Schulte et al.
2005/0053549 A1    3/2005 Parikh et al.
2005/0083527 A1    4/2005 Flaherty et al.
2006/0117763 A1 * 6/2006 Espinosa et al. ............ 62/78

FOREIGN PATENT DOCUMENTS

JP    2-098669 A    4/1990

OTHER PUBLICATIONS

Aylott, Jonathan W. et al.; "Optical Biosensing of Gaseous Nitric Oxide Using Spin-Coated Sol-Gel Thin Films"; 1997, Chem. Mater., vol. 9, pp. 2261-2263.

* cited by examiner

Primary Examiner—Daniel S. Larkin
(74) Attorney, Agent, or Firm—Townsend and Townsend and Crew LLP; Henry Heines

(57) ABSTRACT

The degradation over time that is commonly seen with analyte-binding proteins when used as sensors for trace amounts of an analyte in a gaseous mixture is reduced by maintaining the sensor in a low-oxygen or oxygen-free environment.

28 Claims, 2 Drawing Sheets

TRACE GAS SENSOR WITH REDUCED DEGRADATION

CROSS REFERENCE TO RELATED APPLICATION

This application is a continuation-in-part of U.S. patent application Ser. No. 11/053,046, filed Feb. 7, 2005, now abandoned, and claims priority benefit therefrom for all purposes legally capable of being served thereby. The contents of application Ser. No. 11/053,046 are incorporated herein by reference in their entirety.

BACKGROUND OF THE INVENTION

1. Field of the Invention

This invention resides in the field of sensors for detecting and measuring the concentration of gaseous analytes.

2. Description of the Prior Art

Trace gas analysis is of value in many applications, including the diagnosis and management of physiological conditions. A change in nitric oxide (NO) concentration in the exhaled breath of a person suffering from asthma, for example, can indicate a change in the level of inflammation in the airway of the person, which in turn can indicate an increase in the likelihood of an asthma attack. Another example of a trace gas in exhaled breath that is indicative of an abnormal physiological condition is carbon monoxide. A rise in the carbon monoxide level in exhaled breath can be an early sign of the onset of hemolytic jaundice. A still further example is hydrogen, a rise in which can indicate malabsorption of carbohydrate. In certain cases, these gases are present at concentrations in the parts per billion (ppb) range, and changes within this range can indicate abnormalities before they can be detected at the parts per million range.

Various sensors have been developed to measure the concentrations of different gaseous analytes. Some of these sensors contain bioactive substances, notably proteins, which undergo measurable changes upon contact with gaseous analytes and can therefore be termed "chemical transducers" since they transform the change into a signal that can be read and quantified. One such bioactive substance is cytochrome c, which undergoes an optically quantifiable change in response to NO. Certain sensors that utilize cytochrome c include this protein in encapsulated form in a xerogel (a dry stabilized sol-gel). Sensors of the type and related technology are disclosed in the following U.S. published patent applications and patents: US 2004-0017570 A1, published Jan. 29, 2004 (application Ser. No. 10/334,625, filed Dec. 30, 2002); US 2005-0053549 A1, published Mar. 10, 2005 (application Ser. No. 10/659,408, filed Sep. 10, 2003); US 2005-0083527 A1, published Apr. 21, 2005 (application Ser. No. 10/767,709, filed Jan. 28, 2004); U.S. Pat. No. 5,795,187, issued Aug. 18, 1998; and U.S. Pat. No. 6,010,459, issued Jan. 4, 2000. The disclosures of each of the patents and patent applications listed in this paragraph are hereby incorporated herein by reference.

Unfortunately, certain proteins that are used as trace gas sensors by virtue of detectable changes in the proteins are susceptible to degradation over time. The term "degradation" is used herein to denote a loss in the functionality of the protein, including the responsivity of the protein to the analyte in terms of both the magnitude of the change that can be detected and the time required for the change to occur. In extreme cases, the sensor may have degraded to the point of being useless, i.e., incapable of producing a meaningful or reliable analysis, by the time the user is ready to perform the analysis or even by the time the user obtains a unit containing the sensor. In cytochrome c, for example, a loss of responsivity to NO is evidenced by a loss in the magnitude of the soret peak, which is the spectral peak of the iron porphyrin, the part of the protein that binds NO, and is centered around 400 nm. This degradation has been found to limit the utility of cytochrome c as a sensor in certain circumstances. While the rate of degradation appears to vary with temperature, the mechanism and overall cause of the degradation are unknown. Sensors that display a rapid response are particularly susceptible to degradation. This is true for example in certain cytochrome c elements that are disclosed in the citations above, particularly such elements that are able to generate a signal in less than five minutes of exposure to NO.

SUMMARY OF THE INVENTION

It has now been discovered that the rate of degradation of cytochrome c as a sensor for NO, and other analyte-binding proteins that display degradation over time, can be reduced by controlling the exposure of the protein to oxygen. This is particularly true in the case of cytochrome c-containing sensors that display a rapid response, as stated above. Accordingly, this invention resides in the storage or packaging of the sensor, or the storage or packaging of devices containing the sensor, in a low-oxygen or substantially oxygen-free environment. The term "oxygen" as used in this specification and the appended claims denotes molecular oxygen as opposed to an oxygen atom or atoms covalently bonded to other atoms. The term "low-oxygen environment" refers to oxygen levels that are below the oxygen level in ambient air, i.e., significantly below 21% by volume. Preferred definitions of a low-oxygen environment are 10% or less, 5% or less, and 1% or less, all by volume. The term "substantially oxygen-free" denotes oxygen levels that are either zero or below the limits of detection of the analytical detection method used or available for use in the manufacturing, storage, or shipping environment. Depending on the detection method, the lower detection limit can be 0.1% by volume, 50 ppm by volume, 1 ppm by volume, or 0.1 ppm by volume. In certain embodiments of the invention, the sensor is also maintained in an environment in which the relative humidity is 6% or less, preferably 3% to 6%, and currently 3%. In certain other embodiments of the invention, the relative humidity is maintained at 1% or less, more preferably 0.5% or less, and most preferably 0.1% or less. All values in this paragraph and the appended claims are approximate; the value shown for the digit of the lowest order of magnitude represents a rounded-off value.

DETAILED DESCRIPTION OF THE INVENTION AND PREFERRED EMBODIMENTS

Sensing elements and devices that will benefit from the present invention are those in which the binding species, i.e., the protein that generates the detectable change when contacted with the analyte, is suspended or encapsulated in a solid support matrix to form a sensing element that has a high surface area. Preferred sensing elements are those with a surface area that is greater than 300 m2/g, and most preferred are those with a surface area greater than 390 m2/g. Also preferred are those with a pore width (diameter) of 3 nm to 6 nm, and most preferably 3.5 nm to 5.8 nm. The surface area and pore width are both determined by the BET method well known among those skilled in the art. The matrix itself is preferably a xerogel formed by polymerization of tetramethyl orthosilicate, followed by aging and drying.

Figure 1:
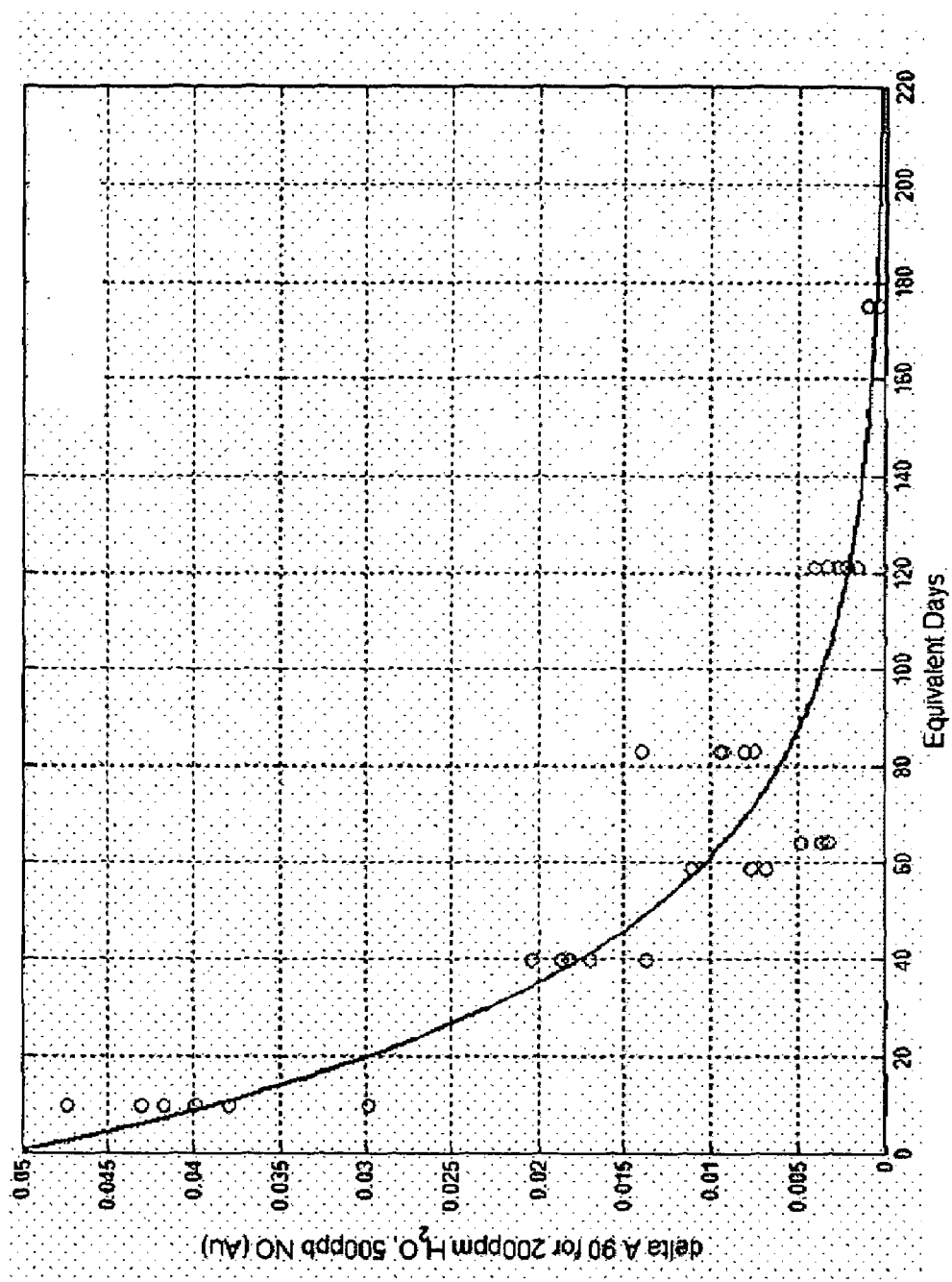
FIG. 1 is a graph showing the degradation over time of a cytochrome c sensor for NO. The y-axis represents the change in absorbance in the sensor after ninety seconds when the humidity in the environment surrounding the sensor is maintained at 200 ppm water and the sensor is reacted with 500 ppb NO. The x-axis represents equivalent days using accelerated aging based on an acceleration model of reaction rate based on measurements of change at 30, 50 and 70 degrees Celsius. The circles represent data points and the solid line represents the Arrhenius-derived decay.
Figure 2:
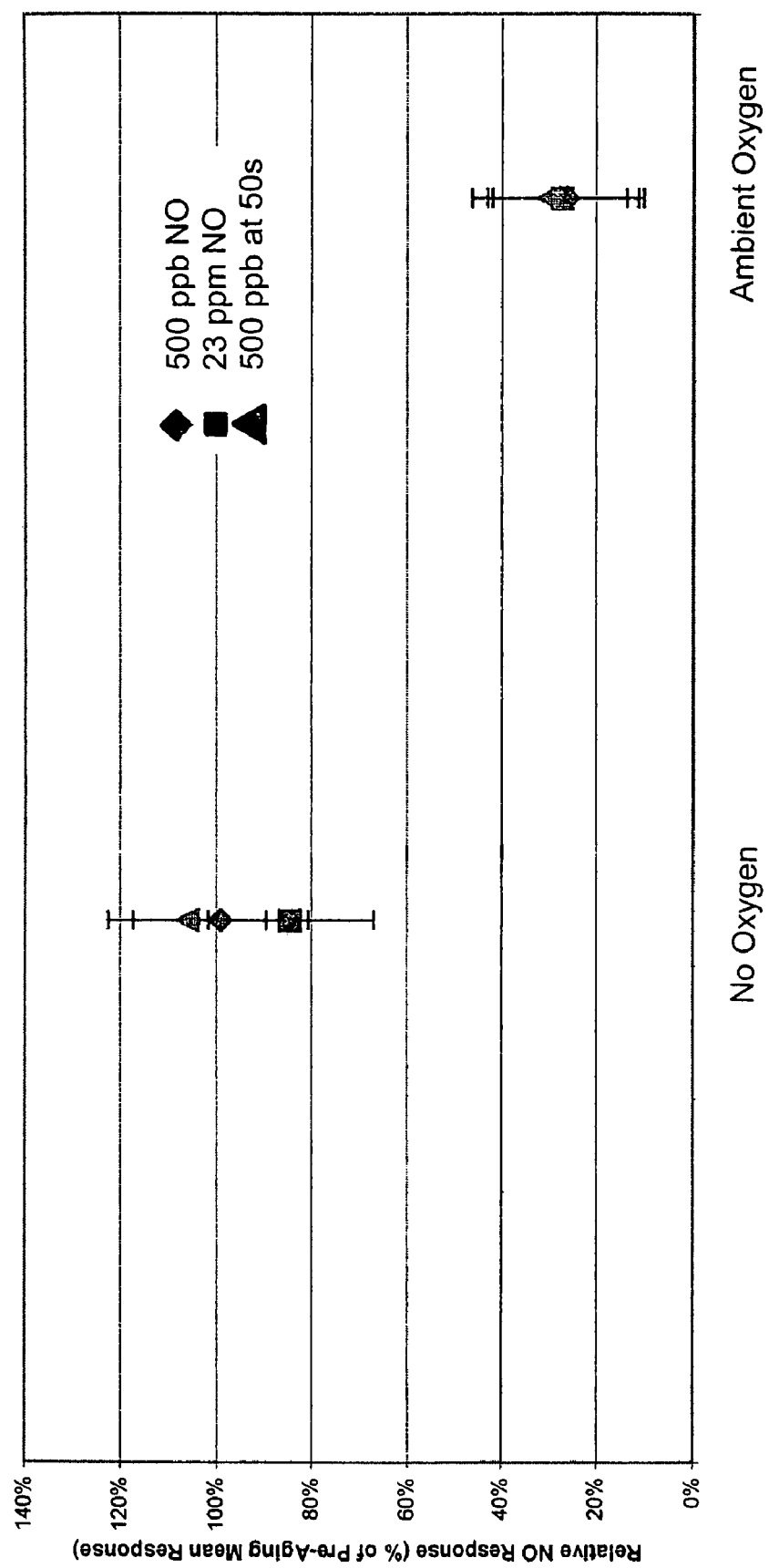
FIG. 2 is a graph comparing the NO response at 70° C. for sensors aged in an ambient environment with the NO response of identical sensors aged under the same conditions except that the environment was oxygen-free. Relative humidity was maintained constant by the use of a 3A molecular sieve. Three sets of data are shown, one representing results obtained from seven days of exposure to 500 ppb NO (diamonds), a second representing results from 7 days of exposure to 23 ppm NO (squares), and the third representing results from fifty seconds of exposure to 500 ppb.

Sensors constructed as described in the three published patent applications referenced above, in which the sensing element was cytochrome c encapsulated in a polymer made from tetramethyl orthosilicate to form a monolith with a surface area of 400 m2/g and a pore width of 5.3 nm, were left in ambient air and exhibited a detectable loss in optical density within twenty-four hours. The accelerated aging test results shown in FIG. 1 indicate that within 120 days essentially all responsivity was lost. When identical sensors were placed in a nitrogen-purged environment and maintained in that environment for the same period of time, the sensors retained all optical density and substantially all responsivity. The results in FIG. 2 indicate that the oxygen-free environment provides results in the retention of essentially full activity in the sensor over seven days for all concentrations of NO in the test.

Experiments were then performed to determine the cause of degradation indicated by the loss of optical density and responsivity. In these experiments, the percentage of degradation was measured in various environmental conditions over a period of the equivalent of 220 days, using an accelerated test. The results are presented in the table below.

Comparative Test Results for a Cytochrome C Monolith

| Environment | Change in sensitivity to 500 ppb NO in air at 220 equivalent days at room temperature (25° C.) as percentage of sensitivity at start of test |
|---|---|
| Relative Humidity: 6%, maintained by saturated solution of LiBr Room temperature (25°), atmospheric pressure Oxygen Atmosphere: Ambient (~21% by volume) | −78% |

-continued

Comparative Test Results for a Cytochrome C Monolith

| Environment | Change in sensitivity to 500 ppb NO in air at 220 equivalent days at room temperature (25° C.) as percentage of sensitivity at start of test |
|---|---|
| Relative Humidity: 0.1%, maintained by a 3A molecular sieve Room temperature (25°), atmospheric pressure Oxygen Atmosphere: No oxygen | −10% |

The first row of data in the table represents the control test, in which a sensor was maintained at an equivalent of room temperature in an environment with an ambient oxygen level at 6% relative humidity, maintained by a saturated solution of LiBr. As indicated in the table, sensitivity was measured by exposing the sensor to air containing 500 ppb NO, both at the start of the test and after 220 equivalent days. By 220 days, the sensitivity had dropped by 78%, i.e., the sensitivity was only 22% of the sensitivity at the start of the test.

The second row of data in the table represents a test in which an identical sensor was again maintained at room temperature but in an environment that was free of oxygen and in which the relative humidity was maintained at 0.1% by a 3 A molecular sieve. Again, using air containing 500 ppb NO as the test composition, the sensor exhibited only a 10% drop in sensitivity, resulting in a sensitivity at the equivalent of 220 days that was 90% of the sensitivity at the start of the test. This confirms that the presence of molecular oxygen was the primary cause of the degradation in the first test, and suggests that the high relative humidity may have further contributed to the degradation.

The degradative effect of oxygen can be controlled in a variety of ways. In one embodiment of the present invention, a low-oxygen or oxygen-free environment can be achieved by purging the sensor housing with nitrogen or another inert gas, and once purged, the housing can be sealed in an oxygen-free, i.e., oxygen-purged, packaging environment. Such purging can for example be achieved with five cycles of nitrogen, based on the volume of the sensor and the volume of the sensor housing. Alternatively, a vacuum can be applied to the housing, either with or without nitrogen purging.

In a second embodiment, the sensor can be sealed in an oxygen-impermeable housing or closure, and an oxygen absorber can be used to remove the oxygen from the housing or closure. An example of such an absorber is CRYOVAC® OS Film (Cryovac Inc., Duncan, S.C., USA). Another are PHARMAKEEP® canisters (Süd-Chemie Performance Packaging, Belen, N.M., USA). The oxygen absorber can be placed in the same packaging as a sealed sensor, particularly when the sealing around the sensor is of oxygen-permeable material that allows oxygen to be drawn through the sealing material by the oxygen absorber. Purging of the sensor housing is optional when an oxygen absorber is used.

An oxygen absorber can also be used to remove oxygen from an unsealed sensor housing, to facilitate the diffusion of oxygen to the absorber.

The foregoing is offered primarily for purposes of illustration. Further embodiments will be readily apparent to those skilled in the art.

What is claimed is:

1. A method for preserving a nitric oxide sensing element in an exhaled breath analyzer against loss of sensitivity during storage, said sensing element comprising a nitric oxide binding protein and said method comprising maintaining said sensing element in a low-oxygen environment or an environment that is substantially free of oxygen.

2. The method of claim 1 wherein said nitric oxide binding protein is cytochrome c.

3. The method of claim 1 wherein said sensing element comprises said nitric oxide binding protein encapsulated in a xerogel.

4. The method of claim 1 wherein said sensing element comprises cytochrome c encapsulated in a xerogel.

5. The method of claim 1 further comprising maintaining said sensing element in an environment in which the relative humidity is 6% or less.

6. The method of claim 1 further comprising maintaining said sensing element in an environment in which the relative humidity is 3% to 6%.

7. The method of claim 1 further comprising maintaining said sensing element in an environment in which the relative humidity is 1% or less.

8. The method of claim 7 wherein said relative humidity is 0.5% or less.

9. The method of claim 7 wherein said relative humidity is 0.1% or less.

10. The method of claim 1 comprising maintaining said sensing element in an environment containing 0.1% oxygen by volume or less.

11. The method of claim 1 comprising maintaining said sensing element in an environment containing 0.1 ppm oxygen by volume or less.

12. The method of claim 1 wherein said sensing element has a surface area that is greater than 300 $m^2/g$.

13. The method of claim 1 wherein said sensing element has a surface area that is greater than 390 $m^2/g$.

14. The method of claim 1 wherein said sensing element comprises cytochrome c encapsulated in a xerogel, has a surface area that is greater than 300 $m^2/g$, and is maintained in an environment containing 0.1% oxygen by volume or less and a relative humidity of 0.1% or less.

15. A device for sensing trace amounts of nitric oxide in exhaled breath, said device comprising a sensing element comprising a nitric oxide binding protein suspended in a support matrix and packaged in an environment that is low in oxygen or substantially free of oxygen.

16. The device of claim 15 wherein said nitric oxide binding protein is cytochrome c.

17. The device of claim 15 wherein said sensing element comprises said nitric oxide binding protein encapsulated in a xerogel.

18. The device of claim 15 wherein said sensing element comprises cytochrome c encapsulated in a xerogel.

19. The device of claim 15 wherein said environment has a relative humidity of 6% or less.

20. The device of claim 19 wherein said relative humidity is 0.5% or less.

21. The device of claim 19 wherein said relative humidity is 0.1% or less.

22. The device of claim 15 wherein said environment has a relative humidity is 3% to 6%.

23. The device of claim 15 wherein said environment has a relative humidity of 1% or less.

24. The device of claim 15 wherein said environment has an oxygen content of 0.1% by volume or less.

25. The device of claim 15 wherein said environment has an oxygen content of 0.1 ppm by volume or less.

26. The device of claim 15 wherein said sensing element has a surface area greater than 300 $m^2/g$.

27. The device of claim 15 wherein said sensing element has a surface area greater than 390 $m^2/g$.

28. The device of claim 15 wherein said nitric oxide binding protein is cytochrome c, said support matrix is a xerogel with a surface area greater than 300 $m^2/g$, and said environment has an oxygen content of 0.1% by volume or less, and a relative humidity of 0.1% or less.

* * * * *